U.S. Patent [19]

Fancher

[11] 4,363,804

[45] Dec. 14, 1982

[54] PHOSPHONODITHIOYLACETYLAMINO PHENYL PYRAZOLES

[75] Inventor: Llewellyn W. Fancher, New Castle, Calif.

[73] Assignee: Stauffer Chemical Company, Westport, Conn.

[21] Appl. No.: 333,201

[22] Filed: Dec. 21, 1981

[51] Int. Cl.³ ..................... A01N 57/24; A01N 57/08; C07F 9/65
[52] U.S. Cl. ..................................... 424/200; 548/119
[58] Field of Search ........................ 548/119; 424/200

[56] References Cited

U.S. PATENT DOCUMENTS

| 4,094,974 | 6/1978 | Fancher | 424/200 |
| 4,104,375 | 8/1978 | Fancher | 424/200 |
| 4,197,295 | 4/1980 | Fancher | 424/200 |

*Primary Examiner*—Alan L. Rotman
*Assistant Examiner*—Natalia Harkaway
*Attorney, Agent, or Firm*—Michael J. Bradley

[57] ABSTRACT

Compounds having the formula

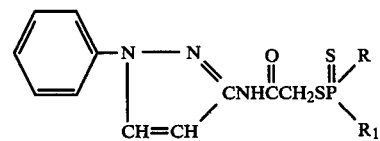

wherein R is lower alkoxy or alkyl having from 1 to 6 carbon atoms, and preferably 1 to 3 carbon atoms and most preferably 1 carbon atom, $R_1$ is lower alkoxy having from 1 to 6 carbon atoms, preferably 2 to 4 carbon atoms, and most preferably 2 carbon atoms, have shown utility as insecticides and miticides.

18 Claims, No Drawings

PHOSPHONODITHIOYLACETYLAMINO PHENYL PYRAZOLES

BACKGROUND OF THE INVENTION

This invention relates to novel compounds having the structural formula

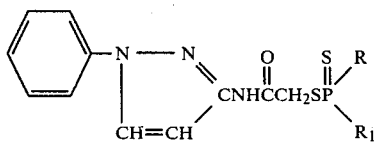

wherein R is lower alkoxy or alkyl having from 1 to 6 carbon atoms, and preferably 1 to 3 carbon atoms and most preferably 1 carbon atom, $R_1$ is lower alkoxy having from 1 to 6 carbon atoms, preferably 2 to 4 carbon atoms, and most preferably 2 carbon atoms. Examples of lower alkyl groups are methyl, ethyl, n-propyl, isopropyl, n-butyl, sec-butyl, i-butyl, and n-amyl. Examples of lower alkoxy groups are methoxy, ethoxy, n-propoxy, isopropoxy, n-butoxy, i-butoxy, n-amyloxy and n-hexoxy.

This invention also relates to a method of controlling or combatting insects or mites by applying an insecticidally or miticidally effective amount of a compound as defined herein to the insect, mite or the habitat thereof, or to a locus at which insecticidal or miticidal protection is desired.

This invention also relates to insecticidal or miticidal compositions of matter comprising an insecticidally or miticidally effective amount of a compound as defined herein with an insecticidally or miticidally suitable diluent or carrier.

DESCRIPTION OF THE INVENTION

The novel compounds that are useful in the practice of this invention are phosphonodithioylacetylamino phenyl pyrazoles having the following structural formula

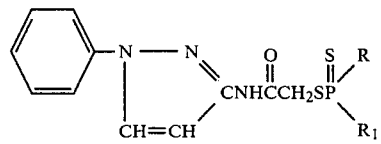

wherein R is lower alkoxy or alkyl having from 1 to 6 carbon atoms, and preferably 1 to 3 carbon atoms and most preferably 1 carbon atom, $R_1$ is lower alkoxy having from 1 to 6 carbon atoms, preferably 2 to 4 carbon atoms, and most preferably 2 carbon atoms.

These compounds are useful as insecticides and miticides alone or when formulated with carriers or other active ingredients.

The novel compounds of this invention can be prepared by the following general procedure:

(1.) Preparation of 5-chloroacetylamino-1-phenylpyrazole 5-amino-1-phenyl pyrazole is reacted with chloroacetic anhydride or chloroacetylchloride at a temperature of from about 25° C. to about 45° C. in a suitable solvent such as tetrahydrofuran, dioxane, dichloromethane and dichloroethane, then refluxed for a suitable period of time.

(2.) Preparation of alkyl-O-alkylphosphonodithioylacetylamino-1-phenyl pyrazole or O,O-dialkyl phosphonodithioylacetylamino-1-phenyl pyrazole The 5-chloroacetylamino-1-phenylpyrazole prepared in step 1 is reacted with an alkyl-O-alkyldithiophosphate or O,O-dialkyldithiophosphate or salts thereof at a temperature below 25° C. in a suitable solvent in the presence of a suitable base to produce the corresponding alkyl-O-alkylphosphonodithioylacetylamino-1-phenyl pyrazole or O,O-dialkylphosphonodialkylacetylamino-1-phenyl pyrazole. Suitable solvents include tetrahydrofuran, dimethyl formamide, dioxane, dichloromethane and dichloroethane. Suitable bases include triethylamine and pyridine. When the salt form of the dithiophosphate is used in the reaction the organic base is not required.

The following examples demonstrate preparation and testing of selected compounds of this invention.

EXAMPLE I

Preparation of 5-Chloroacetyl-1-phenyl pyrazole (intermediate)

In a reaction flask 15.9 grams (g) (0.1 mole) of 5-amino-1-phenyl pyrazole was dissolved in 50 milliliters (ml) of tetrahydrofuran (THF). 22.2 g (0.13 mole) of chloracetic anhydride was added and the mixture was stirred at ambient temperature for 10 minutes during which the temperature rose to 42° C. The reaction mixture was then refluxed on a steam bath for ½ hour and rinco evaporated to a syrupy liquid. The resultant liquid was poured into 150 cc of cold water, made basic with $NaHCO_3$, and extracted with 150 ml $CHCl_3$. The $CHCl_3$ extract was washed with 200 cc dilute NaCl, dried over $MgSO_4$, filtered and rinco evaporated to give 23.8 g (100% of theory) of a viscous liquid having an $n_D^{30}$ of 1.5930 which was identified as the title compound by nuclear magnetic resonance (NMR) spectroscopy.

EXAMPLE II

Preparation of 3-Ethyl-O-ethylphosphonodithioylacetylamino-1-phenyl pyrazole

In a reaction flask 2.89 g (0.017 mole) 3-ethyl,O-ethylphonic acid was mixed with 25 ml dimethylformamide (DMF) with stirring and cooling, neutralized with triethylamine and cooled to below 25° C. 3.53 g (0.015 mole) of the intermediate prepared in Example I was added and the reaction mixture was stirred for 4 hours at ambient temperature. The resultant mixture was poured into 200 ml of water which was then extracted with 200 ml of toluene. The toluene was washed with 100 ml of a dilute NaCl solution, dried over $MgSO_4$, filtered and rinco evaporated to give 4.35 g (79% of theory) of an amber liquid product having an $n_D^{30}$ of 1.5880 which was identified by NMR spectroscopy as the title compound.

TABLE I $$\text{Ph-N=N-CNHCCH}_2\text{SP(=O)(R)(SR}_1\text{)}$$ with CH=CH group (structural diagram of compound with phenyl-N=N, CH=CH, CNHCCH₂SP(O)(S) with R and R₁ substituents)

| Compound No. | | R | R₁ | $n_D^{30}$ |
|---|---|---|---|---|
| R-52428 | 1 | —C₂H₅ | —OC₂H₅ | 1.5880 |
| R-52429 | 2 | —OC₂H₅ | —OC₂H₅ | 1.5755 |
| R-52435 | 3 | —C₂H₅ | —OC₃H₇—i | 1.5723 |
| R-52442 | 4 | —OCH₃ | —OCH₃ | 1.5950 |
| R-52446 | 5 | —C₂H₅ | —OC₄H₉—i | 1.5778 |

The structures of these compounds were confirmed by infrared (IR) and/or nuclear magnetic resonance (NMR) spectral analyses.

Insecticidal Evaluation

The compounds in the above Table I were tested for insecticidal activity against the following insects:
Housefly [*Musca domestica* (Linn.)]
German Cockroach [*Blatella germanica* (Linn.)]
Lygus Bug [*Lygus hesperus* (Knight)]
Black Bean Aphid [*Aphis fabae* (Scop.)]
Green Peach Aphid [*Myzus persicae* (Sulzer)]
Saltmarsh Caterpillar [*Estigmene acrea* (Drury)]
Tobacco Budworm [*Heliothis virescens* (Fabricius)]
Cabbage Looper [*Trichoplusia ni* (Hubner)]
Southern House Mosquito [*Culex pipiens quinquefasciatus* (Say)]

The following testing procedures were used for this evaluation.

Housefly [*Musca domestica*]: Test compounds were diluted in acetone and aliquots pipetted onto the bottom of 55×15 mm aluminum dishes. To insure even spreading of the chemical on the bottom of the dishes, 1 ml of acetone containing 0.02% peanut oil was also added to each dish. After all solvents had evaporated, the dishes were placed in circular cardboard cages containing 25 female houseflies, one to two days old. The cages were covered on the bottom with cellophane and on the top with tulle netting, and each contained a sugar-water saturated cotton plug for maintenance of the flies. Mortality was recorded after 48 hours. Test levels ranged from 100 ug/25 female houseflies down to that at which approximately 50% mortality occurred. The LD-50 values are expressed below in Table II under the heading "HF", in terms of ug of the test compound per 25 female houseflies.

German Cockroach [*Blatella germanica* (Linn.)]: Test compounds were diluted in a 50-50 acetone-water solution. Two cc of the solution was sprayed through a hand spray gun into circular cardboard cages containing 10 one-month old German cockroach nymphs. The test cages were covered on the bottom with cellophane and on the top with tulle netting. Percent mortality was recorded 4 days later. Test concentrations ranged from 0.1% down to that at which approximately 50% mortality occurred. LD-50 values are expressed below in Table II under the heading "GR" in terms of percent of the test compound in the sprayed solution.

Lygus Bug [*Lygus hesperus* (Knight)]: Test compounds were diluted in a 50-50 acetone-water solution. Two cc of the solution were sprayed through a hand spray gun into circular cardboard cages containing 1 green bean pod and 10 adult lygus bugs. The test cages were covered on the bottom with cellophane and on the top with tulle netting. Percent mortality was recorded 48 hours later. Test concentrations ranged from 0.05% down to that at which approximately 50% mortality occurred. LD-50 values are expressed below in Table II under the heading "LB" in terms of percent of the test compound in the sprayed solution.

Black Bean Aphid [*Aphis fabae* (Scop.)]: Nasturtium plants (Tropaeolum sp.) approximately 5 cm tall, were transplanted into sandy loam soil in 3-inch clay pots and infested with 25-50 black bean aphids of mixed ages. Twenty-four hours later they were sprayed to the point of runoff with 50-50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "BA" in terms of percent of the test compound in the sprayed solution.

Green Peach Aphid [*Myzus persicae* (Sulzer)]: Radish plants (*Rhaphanus sativus*), approximately 2 cm tall, were transplanted into sandy loam soil in 3-inch clay pots and infested with 25-50 green peach aphids of mixed ages. Twenty-four hours later they were sprayed to the point of run-off with 50-50 acetone-water solutions of the test chemicals. Treated plants were held in the greenhouse and mortality was recorded after 48 hours. Test concentrations ranged from 0.05% down to that at which 50% mortality occurred. LD-50 values are expressed below in Table II under the heading "GPA" in terms of percent of the test compound in the sprayed solution.

Saltmarsh Caterpillar [*Estigmene acrea* (Drury)]: Test compounds were diluted in a 50-50 acetone-water solution. Sections of curly dock (*Rumex crispus*) leaves, approximately 1×1.5 inches, were immersed in the test solution for 2-3 seconds and placed on a wire screen to dry. The dried leaves were placed in petri dishes containing a moistened piece of filter paper and infested with 5 second-instar saltmarsh larvae. Mortality of the larvae was recorded 48 hours later, and a piece of synthetic medium was added to dishes containing survivors. These were then held for 5 additional days to observe for any delayed effects of the test chemicals.

Test concentrations ranged from 0.05% down to that at which approximately 50% mortality occurred. LD-50 values are expressed below in Table II under the heading "SMC" in terms of percent of the test compound in the solution.

Cabbage Looper [*Trichoplusia ni* (Hubner)]: Test compounds were diluted in a 50-50 acetone-water solution. Cotyledons of hyzini squash (*Calabacita abobrinha*), approximately 1×1.5 inches, were immersed in the test solutions for 2-3 seconds and placed on a wire screen to dry. The dried leaves were placed in petri dishes containing a moistened piece of filter paper and infested with five second-instar cabbage looper larvae. Mortality of the larvae was recorded 48 hours later, and a piece of synthetic media added to dishes containing survivors. These were then held for five additional days to observe for any delayed effects of the test chemicals.

Test concentrations ranged from 0.05% to that at which approximately 50% mortality occurred. LD-50 values are expressed below in Table II under the heading "CL" in terms of percent of the test compound in this solution.

Tobacco budworm [*Heliothis virescens* (Fabricius)]: Test compounds were diluted in a 50-50 acetone-water solution. Sections of Romaine lettuce (*Latuca sativa*) leaves, approximately 1×1.5 inches, were immersed in the test solutions for 2-3 seconds and placed on a wire screen to dry. The dried leaves were placed in petri dishes containing a moistened piece of filter paper and infested with five second-instar tobacco budworm larvae. Mortality of the larvae was recorded 48 hours later, and a piece of synthetic media added to dishes containing survivors. These were then held for five additional days to observe for any delayed effects of the test chemicals.

Test concentrations ranged from 0.05% to that at which approximately 50% mortality occurred. LD-50 values are expressed below in Table II under the heading "TBW" in terms of percent of the test compound in the solution.

Southern House Mosquito Larvae [*Culex pipiens quinquefasciatus* (Say)]: Insecticidal activity was determined using third instar larvae of the mosquito *Culex pipiens quinquefasciatus*. Ten larvae were placed in a six ounce paper cup containing 100 milliliters of an aqueous solution of the test chemical. The treated larvae were stored at 70° F., and 48 hours later the mortality was recorded. Test concentrations ranged from 1.0 ppm down to that at which approximately 50% mortality occurred. LD-50 values are expressed below in Table II under the heading "MOS" in terms of parts per million (ppm) of the test compound in the solution.

Acaricidal Evaluation Test

The two-spotted mite (2SM), *Tetranychus urticae* (Koch), was employed in tests for miticides. The test procedure was as follows:

Pinto bean plants (Phaseolus sp.) approximately 10 cm tall, were transplanted into sandy loam soil in 3-inch clay pots and thoroughly infested with two-spotted mites of mixed ages and sexes. Twenty-four hours later the infested plants were inverted and dipped for 2-3 seconds in 50-50 acetone-water solutions of the test chemicals. Treated plants were held in the greenhouse, and 7 days later mortality was determined for both adult mites and the nymphs hatching from eggs which were on the plants at the time of treatment. Test concentrations ranged from 0.05% down to that at which 50% mortality occurred. LD-50 values are expressed below in Table II under the headings "2SM-PE" (i.e., post-embryonic) and "2SM-Eggs", in terms of percent concentrations of the test compound in the solution.

suspensions, emulsifiable concentrates, flowables, and pastes. Such compositions may contain, in addition to the active compound or compounds, various carriers or diluents; surface active agents (wetting agents, dispersing agents and/or emulsifying agents); solvents (water or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders, flowables and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons with an emulsifying agent. To obtain suspensions or emulsions in water, wetting agents are also added.

It is possible to use highly concentrated liquid compositions containing up to about 95% by weight of the active compound, or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

TABLE II

| Comp. No. | HF, ug | GR % | LB % | BA % | GPA % | SMC % | TBW % | CL % | MOS ppm | 2SM PE % | 2SM EGGS % |
|---|---|---|---|---|---|---|---|---|---|---|---|
| 1 | 100 | >.1 | >0.05 | 0.0007 | 0.0006 | >0.05 | 0.05 | >0.05 | 1 | 0.01 | 0.008 |
| 2 | 100 | >.1 | >0.05 | 0.003 | 0.006 | >0.05 | 0.04 | >0.05 | 1 | <0.05 | <0.05 |
| 3 | <100 >10 | — | — | <0.05 >0.005 | — | — | >0.05 | — | 0.5 | 0.008 | 0.008 |
| 4 | >100 | >.1 | >0.05 | 0.03 | 0.03 | >0.05 | 0.05 | >0.05 | >1 | >0.05 | >0.05 |
| 5 | <100 >10 | >.1 | >0.05 | 0.002 | 0.003 | 0.03 | >0.05 | 0.07 | 0.1 | >0.005 <0.05 | >0.005 <0.05 |

In practice, a pure compound can be used as an insecticide. However, in general, the compounds are first formulated with one or more inert carriers or diluents suitable for insecticidal use, before being applied.

The compositions or formulations, including a compound as described herein, may take and be used in any one of a number of solid or liquid forms. Examples of solid forms are dusts, granules, tablets, powders, and the like. Examples of liquid forms are emulsions, solutions, In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—5 to 90% active compound; aqueous suspensions—10 to 50% active compound; dusts and powders—1 to 25% active compound; granules and pellets—1 to 20% active compound.

The rate of application of the active compound to a locus to be controlled will depend on the nature of the insects to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Control of insect or mite pests is accomplished by applying a composition containing an insecticidally effective amount of an active compound as described herein, to the insect or mite, to a locus at which insecticidal or miticidal control is desired, or to food sources (including seeds) on which the insects or mites feed. For use in the last mentioned manner, it is preferable to utilize a compound which is not volatile. Thus, control may be achieved by direct application of the active compounds to the insects and indirectly by application of the compounds to a locus to be protected (such as crop lands, grass ranges, and forests), to a source of food for insects or to other insect habitats (for example, breeding or swarming areas). The rates of application of the active compound, and the concentration applied, will vary according to whether the compound or composition is being directly applied to the insect or indirectly, to a locus, food or habitat. In the latter case the rate of the application, depending on the nature of the insects or mites to be controlled, and the plant environment, will generally vary from about 0.01 to about 100 pounds per acre (about 0.011 to about 112 kg/ha.)

What is claimed is:

1. A compound having the structural formula

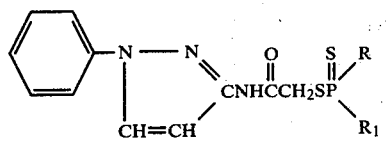

wherein R is lower alkoxy or alkyl having from 1 to 6 carbon atoms and $R_1$ is lower alkoxy having from 1 to 6 carbon atoms.

2. The compound of claim 1 wherein R is —$C_2H_5$ and $R_1$ is —$OC_2H_5$.

3. The compound of claim 1 wherein R is —$OC_2H_5$ and $R_1$ is —$OC_2H_5$.

4. The compound of claim 1 wherein R is —$C_2H_5$ and $R_1$ is —$OC_3H_7$—i.

5. The compound of claim 1 wherein R is —$OCH_3$ and $R_1$ is —$OCH_3$.

6. The compound of claim 1 wherein R is —$C_2H_5$ and $R_1$ is —$OC_4H_9$—i.

7. A composition of matter comprising
(a) an insecticidally or miticidally effective amount of a compound having the structural formula

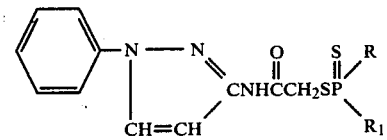

wherein R is lower alkoxy or alkyl having from 1 to 6 carbon atoms, and $R_1$ is lower alkoxy having from 1 to 6 carbon atoms, and
(b) a suitable inert carrier or diluent.

8. The composition of claim 7 wherein R is —$C_2H_5$ and $R_1$ is —$OC_2H_5$.

9. The composition of claim 7 wherein R is —$OC_2H_5$ and $R_1$ is —$OC_2H_5$.

10. The composition of claim 7 wherein R is —$C_2H_5$ and $R_1$ is —$OC_3H_7$—i.

11. The composition of claim 7 wherein R is —$OCH_3$ and $R_1$ is —$OCH_3$.

12. The composition of claim 7 wherein R is —$C_2H_5$ and $R_1$ is —$OC_4H_9$—i.

13. A method for controlling insects or mites comprising applying to the insects, the habitat thereof, or a locus where protection is desired, an insecticidally or miticidally effective amount of a compound having the formula

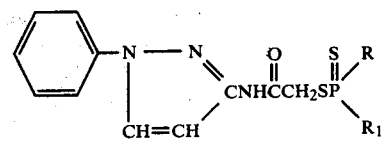

wherein R is lower alkoxy or alkyl having from 1 to 6 carbon atoms, and $R_1$ is lower alkoxy having from 1 to 6 carbon atoms.

14. The method of claim 13 wherein R is —$C_2H_5$ and $R_1$ is —$OC_2H_5$.

15. The method of claim 13 wherein R is —$OC_2H_5$ and $R_1$ is —$OC_2H_5$.

16. The method of claim 13 wherein R is —$C_2H_5$ and $R_1$ is —$OC_3H_7$—i.

17. The method of claim 13 wherein R is —$OCH_3$ and $R_1$ is —$OCH_3$.

18. The method of claim 13 wherein R is —$C_2H_5$ and $R_1$ is —$OC_4H_9$—i.

* * * * *